United States Patent [19]

McCarroll et al.

[11] 4,122,040
[45] Oct. 24, 1978

[54] PLATINUM GROUP METAL CATALYST

[75] Inventors: John James McCarroll, Camberley; John Trevor Kent Clark, Weybridge; Stephen Robert Tennison, New Haw, all of England

[73] Assignee: The British Petroleum Company Limited, London, England

[21] Appl. No.: 725,587

[22] Filed: Sep. 22, 1976

Related U.S. Application Data

[63] Continuation-in-part of Ser. No. 606,420, Aug. 21, 1975, abandoned.

[30] Foreign Application Priority Data

Sep. 2, 1974 [GB] United Kingdom ............... 38182/74
Sep. 2, 1974 [GB] United Kingdom ............... 38183/74

[51] Int. Cl.$^2$ ............................................. B01J 21/18
[52] U.S. Cl. .................................... 252/447; 252/441; 260/667; 260/673.5; 260/683.9
[58] Field of Search ..................... 252/447, 444, 441

[56] References Cited

U.S. PATENT DOCUMENTS

| 3,663,166 | 5/1971 | Weise et al. | 252/447 X |
| 3,830,753 | 8/1974 | Ichikawa et al. | 252/447 X |
| 3,853,786 | 12/1974 | Forni et al. | 252/447 X |

Primary Examiner—Patrick Garvin
Attorney, Agent, or Firm—Morgan, Finnegan, Pine, Foley & Lee

[57] ABSTRACT

Hydrogen transfer catalyst comprises (a) as support a graphite containing carbon having (1) a basal plane surface area of at least 100 m$^2$/g, (2) a ratio of BET surface area to basal plane surface area of not more than 5:1 and (3) a ratio of basal plane surface area to edge surface area of at least 5:1 and (b) as active component, 0.01 to 10% by weight, of the total weight of catalyst of a platinum group metal disposed thereon. The catalyst is particularly suitable for reforming.

10 Claims, No Drawings

PLATINUM GROUP METAL CATALYST

This application is a continuation-in-part of application Ser. No. 606,420, filed Aug. 21, 1975, now abandoned.

This invention relates to a novel supported platinum group metal catalyst and to its use. The catalyst is particularly suitable for use in hydrogen transfer reactions such as the hydrogenation, dehydrogenation and/or dehydrocyclisation of hydrocarbons.

Our copending application Ser. No. 725,586, filed Sept. 22, 1976, now U.S. Pat. No. 4,055,628 discloses a method for preparing graphite-containing carbon having (1) a basal plane surface area of at least 100 m$^2$/g, (2) a ratio of BET surface area to basal plane surface area of not more than 5:1 and (3) a ratio of basal plane surface area to edge surface area of at least 5:1, which method comprises the steps of (1) an initial heat treatment in an inert atmosphere at a temperature between 900° and 3300° C, (2) an oxidation stage at a temperature between 300° C and 1200° C and (3) a further heat treatment in an inert atmosphere at a temperature between 1000° C and 3000° C, preferably 2000° C.

Preferably the carbon initially has a BET surface area in the range 100 to 3000 m$^2$/g.

In Steps (1) and (3) nitrogen provides a suitable atmosphere for temperatures up to 1000° C. Above this, an inert gas, e.g., argon or helium, should preferably be used. In Step (2) suitable oxidising media include air, steam and carbon dioxide. If air is employed, the temperature is preferably in the range 300° to 450° C; if steam or carbon dioxide, in the range 800°–1200° C.

During the heating in the inert atmosphere a portion at least of the carbon is converted to graphite, and it is believed that adsorbed organic oxygen-containing groups such as ketones, hydroxyl, carboxylic acids and the like are removed. The absence of organic oxygen containing groups from the treated carbon (less than 1%) is believed to be significant in the context of selectivity of the catalyst employing the carbon as a support, since oxygen-containing groups have been reported to promote side reactions.

The graphite containing carbon comprises a crystalline layered structure in which the constituent atoms form layers attached to each other by relatively weak Van der Waals dispersion forces. The crystalline surface area of the material is formed largely of the basal planes of the layers with a smaller contribution from the edges of the layers. There will usually be some amorphous carbon associated with the crystalline material.

The basal surface area is determined by measuring the heat of adsorption of n-dotriacontane from n-heptane. Similarly the edge surface area is determined by the heat of adsorption of n-butanol from n-heptane.

Heats of adsorption can be measured using a flow microcalorimeter as described in "Chemistry and Industry" for Mar. 20, 1965 at pages 482–485.

The BET surface area is the surface area determined by the nitrogen adsorption method of Brunauer, Emmet and Teller disclosed in J. Am. Chem. Soc. 60, 309, (1938). This corresponds to the total surface area, i.e., the crystalline basal plane surface area, the crystalline edge surface area and the amorphous surface area.

We have now discovered that the graphite-containing carbon can be used as a support for platinum group metals and that the supported metal catalysts are effective for hydrogen transfer reactions.

Thus according to the present invention there is provided a catalyst comprising (a) as support, a graphite containing carbon having (1) a basal plane surface area of at least 100 m$^2$/g, (2) a ratio of BET surface area to basal plane surface area of not more than 5:1 and (3) a ratio of basal plane surface area to edge surface area of at least 5:1 and (b) as active component, 0.01 to 10% by weight, preferably 0.1 to 5% by weight, of the total weight of catalyst, of a platinum group metal disposed thereon.

By "platinum group metal" we mean ruthenium, rhodium, palladium, osmium, iridium, platinum and gold.

The preferred metals are platinum itself and iridium.

Preferably the basal plane surface area is at least 150 m$^2$/g. If the basal plane area is greater than 1000 m$^2$/g, the material is unlikely to have sufficient strength for a catalyst support.

The closer that the ratio of the BET surface area to the basal plane area is to the theoretical minimum of 1, the higher is the quality of the material, i.e., the higher is the proportion of crystalline material and the lower is the proportion of amorphous.

Perferably the ratio of the basal plane surface area to the edge surface area is greater than 10:1, most preferably greater than 300:1.

Preferably the graphite containing carbon has a pH in the range from 5 to 9, more preferably from 6 to 8, most preferably about 7, and contains less than 1% by wt. of adsorbed oxygen, more preferably less than 0.5% by wt. of adsorbed oxygen. The lower the proportion of adsorbed oxygen, the closer is the pH to 7.

Preferably the total metals content of the graphite containing carbon is less than 250 ppm. Preferably the graphite containing carbon contains less than 200 ppm, more preferably less than 100 ppm of alkali and alkaline earth metals.

The particle size of the graphite containing carbon is not significant and can be controlled in known manner in view of its intended application, ranging from fine particles for use in slurry processes to granules for use in fixed bed processes.

The graphite may be prepared from many different forms of carbon, including (a) activated carbons derived from coconut charcoal, coal, peat, etc. (b) carbons produced by the coking of petroleum residues, and (c) oleophilic graphite, e.g., as prepared according to out British Patent Specification No. 1168785.

Preferably the carbon employed as a starting material is one which, prior to heat treatment as above, at approximately 1000° C, has a BET surface area of at least 500 m$^2$lg.

The preparation of the graphite containing carbon varies according to the type of carbon selected and utilises combinations of heat treatment under inert and oxidising conditions chosen so as to optimise the ratios of BET to basal plane areas and basal plane to edge surface areas.

Heating in an inert atmosphere increases the proportion of graphitic material, i.e., decreases the first ratio and increases the second. With most forms of carbon, however, the total surface area is significantly reduced by this treatment, but this is not always the case and some forms of carbon show only a relatively small decrease in surface area on heating.

Oxidation under carefully controlled conditions, by contrast, increases the surface area.

The graphite containing carbon as defined above can be employed as a catalyst support for a large number of metals or metal-containing compound catalysts for a wide range of reactions. Because the carbon is very inert the metal or metal containing catalyst exhibits the catalytic properties of the metal.

The catalyst is prepared by impregnating the graphite-containing carbon support with a solution of a reducible platinum group metal compound and reducing the reducible compound to the metal.

Suitable solutions include aqueous solutions of tetrammine platinous chloride, platinum tetrammine hydroxide and chloroplatinic acid. Suitable conditions for the impregnation are temperature of 20° to 90° C, times of 1 to 6 hours and solution concentrations of $10^{-4}$ to 1 molar.

After the impregnation the catalyst may be dried at, e.g., 100°–250° C, for 1 - 24 hours.

Preferably the catalyst composition also contains a minor proportion of a modifying metal ion selected from the alkali and alkaline earth metal ions. The modifying metal ion gives a marked increase in the dehydrocyclisation activity of the platinum group metal. The preferred quantity of modifying metal is from 10 to 300 atomic percent of the platinum group metal. Any alkali metal is suitable but the preferred one is sodium. The alkaline earth metal can be magnesium, calcium, strontium or barium.

The quantity of modifying metal ion which can be added to the catalyst is much greater when the latter has been prepared from chloroplatinic acid or similar compounds than when it has been prepared from a tetrammine complex. Maximum activity can be maintained up to about 300 atomic percent for the former and up to about 150 atomic percent for the latter.

The platinum group metal is preferably reduced before use, e.g., by heating to 200° to 700° C, preferably 300°–600° C, for 1 to 5 hours in a reducing atmosphere, preferably a stream of hydrogen flowing at from 500 to 10,000 v/v/hr. The alkali or alkaline earth metal ion is preferably added before the reduction of the platinum group metal.

The catalyst is particularly suitable for the dehydrocyclisation of acyclic straight chain hydrocarbons having at least 6 carbon atoms or other hydrocarbons having in their structure a straight chain with at least 6 carbon atoms which is capable of cyclisation. The preferred hydrocarbons are paraffins, although olefins may be used. Particularly suitable feedstocks are $C_{6-10}$ paraffin hydrocarbons which will give benzene and/or lower alkyl aromatics in good yield with a minimum of side reactions. The feedstocks may be pure hydrocarbons, or mixtures of acyclic hydrocarbons. Such mixtures may also contain naphthenes and aromatics and may be, for example, petroleum fractions, particularly those boiling in the range 60°–250° C.

Sulphur compounds are normally undesirable in feedstocks for platinum group metal catalysts and preferably the sulphur content of the feedstock is less than 10 ppm (wt), more particularly, less than 1 ppm (wt.).

Thus according to a further aspect of the present invention there is provided a hydrocarbon hydrogen transfer process which process comprises contacting the hydrocarbons under conversion conditions with a catalyst as hereinbefore defined.

Broad and preferred ranges of process conditions for dehydrogenation and/or dehydrocyclisation are as follows

|  |  | Broad Range | Preferred Range |
|---|---|---|---|
| Temperature | °C | 200–650 | 400–600 |
| Pressure | bars(ga) | 1–210 | 1–70 |
| Space Velocity | v/v/hr | 0.01–20 | 0.1–10 |
| $H_2$: hydrocarbon mole ratio |  | 0.01:1–20:1 | 0.5:1–10:1 |

The catalyst is also suitable for use in hydrogenating aromatic compounds such as benzene and other compounds such as olefins and acetylenes.

Broad and preferred ranges of process conditions for hydrogenation are as follows:

|  |  | Broad Range | Preferred Range |
|---|---|---|---|
| Temperature | °C | 0–400 | 100–300 |
| Pressure | bars(ga) | 1–210 | 1–70 |
| Space Velocity | v/v/hr | 0.01–20 | 0.1–10 |
| $H_2$: hydrocarbon mole ratio |  | 0.01–20:1 | 0.5:1–10:1 |

The invention is illustrated with reference to the following Examples, of which Examples 4, 7 and 8 are not according to the invention and are included for comparative purposes only.

EXAMPLE 1

Preparation of the carbon 45 gms of carbon black sold by the Cabot Corporation under the Trade Name "Black Pearls 71" was heated under an atmosphere of nitrogen to 1000° C to remove volatile matter and allowed to cool to room temperature (wt. loss 11.4%). The sample was then heated in an atmosphere of argon from room temperature to 2700° C which temperature was maintained for about 30 minutes, and then allowed to cool (further wt loss 2.3%). This second heating and cooling treatment lasted about 3 hours. After cooling the carbon had a black and grey mottled appearance and

| BET surface area | 180 m²/g |
|---|---|
| Basal surface area | 150 m²/g |
| Edge surface area | 0.36 m²/g |
| BET/Basal ratio | 1.2:1 |
| Basal/Edge ratio | 427:1 |
| pH | 7 (measured by slurrying with water) |
| % graphite | 30% by wt. (X-ray diffraction) |
| % amorphous carbon | 70% by wt. |
| total metals content | 13 ppm |
| ash content | zero |
| % adsorbed oxygen | zero |

As a result of the heat treatments the total weight loss was 13.7% wt.

The carbon was in the form of spheres 200–400A in diameter which are believed to have an outer graphite skin.

Preparation of catalyst 0.7% wt. of platinum was added to the support by impregnating with a 1/10 molar aqueous solution of $Pt(NH_3)_4(OH)_2$ at 90° C for 4 hours, followed by drying at 120° C for 2 hours.

A portion of this impregnated material was then further impregnated with an aqueous solution of sodium carbonate containing 0.74 gms per liter, at 90° C for 2 hours, following by drying at 110° C for 2 hours, sieving to 40–100 BSS mesh granule size and then reducing at 500° C for 2 hours in a stream of hydrogen flowing at 4000 v/v/hour. The resulting catalyst contained 600 parts per million of sodium, corresponding to 73 atomic % of the platinum.

During the impregnation of platinum and sodium and the subsequent removal of water, the catalyst was continuously agitated to ensure even distribution of both components within and between catalyst pellets.

Use of the carbon prepared as described above as a catalyst support (i) 0.225 gms of the catalyst was used for the dehydrocyclization of n-hexane at 500° C in a microreactor at atmospheric pressure using a molar ratio of hydrogen:n-hexane of 7:1 and a liquid space velocity of 4 v/v/hour. The microreactor had a capacity for 0.45 ml catalyst.

(ii) a portion of the catalyst prepared as described above but omitting the sodium addition step was also tested under the same conditions. The results are recorded below.

|  | No added sodium | 600 ppm sodium |
|---|---|---|
| % Activity | 63 | 92 |
| % Benzene | 38 | 72 |

A sample of carbon black sold by the Cabot Corporation under the Trade Name "Black Pearls 2" was heated in two stages as described in Example 1 above and allowed to cool (total wt. loss 32%wt).

After cooling, the carbon had a black and grey mottled appearance and

| BET surface area | 235 m$^2$/g |
|---|---|
| Basal surface area | 230 m$^2$/g |
| Edge surface area | 0.3 m$^2$/g |
| BET/Basal ratio | 1.02:1 |
| Basal/Edge ratio | 766:1 |
| pH | 7 |
| total metals content | 13 ppm |
| ash content | zero |
| % adsorbed oxygen | zero |
| % graphite | 30% |
| % amorphous carbon | 70% |

A catalyst containing 0.7% by wt platinum and 600 ppm sodium was prepared by treating the above support as described in Example 1.

(i) n-hexane was dehydrocyclised as in Example 1.

(ii) a portion of the catalyst prepared as described but omitting the sodium addition step was also tested under the same conditions. The results are recorded below

|  | No added sodium | 600 ppm sodium |
|---|---|---|
| % Activity | 75 | 98 |
| % Benzene | 46 | 85 |

EXAMPLE 3

The sodium containing catalyst described in Example 2 was employed for the dehydrocyclisation of n-hexane to benzene over a period of 42 hours on stream under the processing conditions of Example 1.

During the run the results obtained were as set out overleaf.

| Hours on Stream | % Activity | % Selectivity to Benzene | % Benzene Yield |
|---|---|---|---|
| 2 | 92.5 | 78.0 | 76.0 |
| 20 | 80.0 | 76.0 | 60.0 |
| 30 | 77.0 | 67.5 | 52.5 |
| 42 | 72.0 | 63.0 | 46.0 |

EXAMPLE 4

A number of different commercially available dehydrocyclisation catalysts were tested under the processing conditions of Example 1 and their activity and benzene yield compared with those of the sodium containing catalyst described in Example 2.

The results are set out below

|  | % Activity | % Benzene Yield |
|---|---|---|
| 0.45 gms (0.45 ml) of a commercially available reforming catalyst containing 0.35% Pt on Al$_2$O$_3$ | 56.0 | 18.5 |
| 0.45 gms (0.45 ml) of a commercially available reforming catalyst containing Pt and Re on Al$_2$O$_3$ | 66.0 | 19.5 |
| 0.45 gms (0.45 ml) of a commercially available reforming catalyst containing 0.35% Pt on Al$_2$O$_3$ and containing chlorine | 41.0 | 12.0 |

EXAMPLE 5

A sodium doped catalyst similar to that of Example 2 was employed to hydrogenate benzene at various temperatures and atmospheric pressure in the microreactor using a molar ratio of hydrogen to hydrocarbon of 6:1 and a liquid space velocity of 1 v/v/hour. Instead of being reduced at 500° C for 2 hours it was reduced at 250° C for half an hour.

The following conversions were achieved:

| Temperature ° C | Conversion % |
|---|---|
| 150 | 100 |
| 100 | 100 |
| 85 | 100 |
| 70 | 34.6 after 3 hours on stream |

EXAMPLE 6

A catalyst similar to that of Example 5 was employed to hydrogenate benzene under the same conditions and at 75° C. In this example the catalyst was reduced at 225° C for ¼ hour.

The following conversions were achieved:

| Time (minutes) | Conversion % |
|---|---|
| 5 | 96.3 |
| 20 | 100 |
| 60 | 100 |

EXAMPLE 7

Example 5 was repeated using a commercially available reforming catalyst containing 0.35% Pt on alumina which had been reduced at 250° C for 1½ hours.

The following conversions were achieved.

| Temperature °C | Conversion % |
|---|---|
| 150 | 100 |
| 100 | 11.5 |
| 85 | 5.9 |

EXAMPLE 8

Example 7 was repeated using a commercially available reforming catalyst containing 0.35% Pt on alumina which had been reduced at 500° C for 1½ hours.

The following conversions were achieved

| Time (minutes) | Conversion % |
|---|---|
| 5 | 94.9 |
| 20 | 82.3 |
| 60 | 33.5 |

It will be noted that all hydrocarbon conversions were carried out in a microreactor with a capacity for 0.45 ml catalyst. This volume is equivalent to 0.225 g catalyst based on graphite-containing carbon and 0.45 g catalyst based on alumina. Thus in order to ensure comparable platinum contents within the reactor it is necessary to load the carbon based catalyst with twice as much platinum as the alumina based catalyst.

EXAMPLE 9

Activated carbon AC40, supplied by CECA Ltd., was heat-treated to 900° C in nitrogen (to remove undesirable aromatic residues) and the heat treatment continued to 1500° C in argon. The resultant carbon was then, in a second step, oxidised in air at 425° C to 23 percent weight loss. This oxidised carbon was then, in the third step, reheat-treated to 1900° C or 1700° C in argon. The resultant carbons at each stage were then ground to 16–30 mesh BSS and impregnated with 1.0 percent weight Pt using a dilute solution of $H_2PtCl_6$. The catalyst was reduced in flowing hydrogen and then used to dehydrocyclise n-hexane at 500° C, 2 LHSV of n-$C_6$, 10:1 $H_2$:HC, at 1 atms total pressure.

The surface areas of the carbons produced at the various stages were: As received $N_2$ BET area m²/g 1260

|  | 1st Step (to 1500° C) | 2nd Step (burn-out in air) | 3rd Step (reheat-treated to 1900° C) | 3rd Step (to 1700° C) |
|---|---|---|---|---|
| $N_2$ BET area m²/g | 565 | 1107 | 310 | 539 |
| Basal area m²/g | 278 | 476 | 202 | 312 |
| Edge area m²/g | 11 | 56 | 0.4 | 2.4 |

A typical measure of the strength of the catalyst after the final stages is a mean piece crushing strength of 0.87 kg/mm.

The results of the n-hexane dehydrocyclisation tests after 60 minutes on stream were:

|  | 1st Step (to 1500° C) | 2nd Step (burn-out) | 3rd Step (to 1900° C) | 3rd Step (to 1700° C) |
|---|---|---|---|---|
| Conversion of n-$C_6$ | 30.4 | 40.0 | 59.5 | 40.2 |
| Benzene yield | 10.9 | 13.8 | 35.4 | 17.2 |
| Selectivity | 35.9 | 34.7 | 59.5 | 42.9 |

This clearly demonstrates the effects of heat treatment on production of the specific surfaces and the effect of these surfaces influencing the catalytic behaviour.

We claim:

1. A catalyst comprising (a) as support, a graphite-containing carbon having (1) a basal plane surface area of at least 100 m²/g, (2) a ratio of BET surface area to basal plane surface area of not more than 5:1 and (3) a ratio of basal plane surface area to edge surface area of at least 5:1 and (b) as active component, 0.01 to 10% by weight of a platinum group metal disposed thereon.

2. A catalyst according to claim 1 wherein the active component is present in amount 0.1 to 5% by weight.

3. A catalyst according to either of claims 1 or 2 wherein the platinum group metal is platinum or iridium.

4. A catalyst according to claim 1 wherein the basal plane surface area is in the range 150 m²/g to 500 m²/g.

5. A catalyst according to claim 1 the ratio of the BET surface area to the basal plane surface area is in the range 2:1 to 1.01:1.

6. A catalyst according to claim 1 wherein the ratio of the basal plane surface area to the edge surface area is greater than 50:1.

7. A catalyst according to claim 6 wherein the ratio of the basal plane surface area to the edge surface area is greater than 300:1.

8. A catalyst according to claim 1 wherein the catalyst contains a modifying metal ion selected from the alkali and alkaline earth metal ions.

9. A catalyst according to claim 8 wherein the modifying metal ion is present in amount 10 to 300 atomic percent of the platinum group metal.

10. A catalyst according to claim 9 wherein the modifying metal ion is sodium.

* * * * *